United States Patent [19]

Anspach, III et al.

[11] Patent Number: 5,725,541
[45] Date of Patent: Mar. 10, 1998

[54] SOFT TISSUE FASTENER DEVICE

[75] Inventors: William E. Anspach, III, Stuart; Eddy H. Del Rio, Royal Palm Beach, both of Fla.

[73] Assignee: The Anspach Effort, Inc., Palm Beach Gardens, Fla.

[21] Appl. No.: 806,733

[22] Filed: Feb. 27, 1997

Related U.S. Application Data

[63] Continuation-in-part of Ser. No. 589,779, Jan. 22, 1996.
[51] Int. Cl.⁶ .................................................. A61B 17/00
[52] U.S. Cl. .................... 606/151; 606/73; 606/232; 411/34; 411/59
[58] Field of Search .................... 606/148, 151, 606/139, 232, 72, 73, 75; 411/34, 43, 36–38, 59–61

[56] References Cited

U.S. PATENT DOCUMENTS 4,790,304  12/1988  Rosenberg ........................ 606/72
4,859,128  8/1989  Brecz et al. ...................... 411/43
5,013,316  5/1991  Goble et al. ...................... 606/75
5,501,695  3/1996  Aspach, Jr. et al. ............. 606/232

*Primary Examiner*—Jeffrey A. Schmidt
*Attorney, Agent, or Firm*—Norman Friedland; Jack N. McCarthy

[57] ABSTRACT

An expandable fastener device for attaching tissue to bone and a surgical operating technique for using it. The fastener device includes a shaft which will pierce tissue and when rotated, will drill a hole in bone with a drill point to receive the fastener in bone. The device can be drilled in place and fixed in place by actuation of the device itself. The anchor porion of the fastener device remaining in the body when the shaft is sheared and removed, is made from a a bioabsorbable polymer material and an implantable grade titanium material or alloy thereof. The portion of the fastener that captures the body soft tissue (tendon or ligaments) is biodegradable and the portion anchored to the bone is the titanium material. Another embodiment constructs the component that captures the body soft tissue into a pedal-like integral disk where each pedal flexes to conform to the shape of the bone surface adjacent thereto.

15 Claims, 11 Drawing Sheets

SOFT TISSUE FASTENER DEVICE

This is a continuation-in-part patent application of U.S. patent application Ser. No. 08/589,779 filed on Jan. 22, 1996.

DESCRIPTION

1. Technical Field

This invention relates to a device and technique for attaching soft tissues to bone during surgery and particularly to utilizing bioabsorbable material in judicious location in the device.

2. Background Art

Frequently during traumatic events, soft tissues are avulsed from their bony attachments. Common means of reattaching soft tissues such as tendons or ligaments to bone during surgery include the use of staples, tacks, screws with spiked washers, sutures passed through drill holes in the bone or sutures passed through devices implanted beneath the bone's surface (suture anchors). Staples and tacks are simple to use but have relatively poor holding strength, which can be a problem when they are placed near a moving joint and therefore subjected to stress. Screws, suture anchors and sutures passed through drill holes have good fixation strength but require multiple surgical steps such as exposing the bone, drilling a hole, piercing the soft tissue, tying the suture, etc.

A suture anchor is shown in U.S. Pat. Nos. 5,102,421; 5,167,665; 5,326,205; and application Ser. No. 08/215,279, filed Mar. 21, 1994 which is a continuation-in-part of the application which issued as U.S. Pat. No. 5,326,205.

As is well known in this technology it is abundantly important that implants that remain in the body of the patient must not provide a source of irritation or traumatize the body. Under certain conditions, it has been found that the components of the rivet types of devices could result in a protrusion extending beyond the bone structure of the body and obviously, could be in a location that could result in irritation of the ligaments or tendons.

SUMMARY OF THE INVENTION

The object of the present invention is to credit a self-drilling, expandable, "blind" rivet-like fastener device that attaches soft tissues (tendons, ligaments) to bone. The expanding fastener device gives firm fixation to bone and the drilling feature eliminates the need for pre-drilling a hole. The fastener device is made up of several components such that the components that remain in the body include a surgical titanium rivet-like or anchor component and a bioabsorbable support structure that will dissolve in a given period of time and avoid the potential of projecting beyond the bone structure of the body of the patient.

The fastener device has four functional parts:

1. An annular fastener body which, when compressed, deploys wings or arms for securing the fastener body to the bone beneath the surface of the bone;

2. A rotatable or swivel head which is attached to the top of the fastener body; the head captures the soft tissue to the surface of the bone;

3. A drill and puller shaft extends through the annular fastener body with a drill point below said annular fastener body which impales the soft tissue and when rotated, drills a hole in a bone into which the fastener body can advance to a desired position with the rotatable head against the soft issue, pressing it to the surface of the bone.

4. A thrust adapter assembly extends around the drill and puller shaft from the top of said annular fastener body to below the top of the drill and puller shaft to permit the thrust adapter assembly and drill and puller shaft to be rotated without rotation and said rotatable head and fastener body. The thrust adapter provides support for the drill and puller shaft during drilling, and resists bending thereof. When moved to a desired position, a surgical fastener puller instrument is placed over the free end of the drill and puller shaft and placed against the top of the thrust adapter assembly. The instrument grasps the drill and puller shaft and pulls it upwardly to have the top of the drill point react with the bottom of the cylindrical fastener body while the bottom of the thrust adapter assembly holds the top of the cylindrical fastener body against axial movement. This action compresses the fastener body to cause the wings or arms to deploy radically outwardly into the bone. The drill and puller shaft breaks off at a desired point when resistance to pulling is great enough.

Another object of the invention is to create a unique surgical technique. During this procedure, the soft tissue is pierced by the fastener device and captured by the head of the device. The drill point is then placed against the bony surface. The drill point of the fastener device is made to rotate, causing a hole to be formed, the drill point therefore forms the hold, drawing the captured soft tissue to the bone surface. The fastener is then caused to expand into the bone beneath bone surface, thereby securing it in position within the bone. The soft tissue, which lies between the portion of the device within the bone and the head of the device external to the bone is thereby secured against the bone surface.

A unique feature of the present invention includes use of the fastener body as a sleeve to protect the captured soft tissue from the rotating drill and puller shaft. The fastener body, and drill and puller shaft, are fitted together, such that the drill and puller shaft rotates within the fastener body without causing simultaneous rotation of the fastener body. This independent rotation avoids damage to the captured soft tissue which could be caused by direct contact with a rotating surface of the fastener.

Another unique feature is a "toggling washer" type of fastener head. This type of fastener head allows the fastener body to be placed into the bone surface yet still holds the soft tissues uniformly flat on the bone surface. It may be of varying shapes and dimensions and may also be made of material dissimilar to the fastener body, such as plastic or a biodegradable or absorbable material.

Besides the intended application in the medical field, the "blind" fastener device has potential application in industry. For example, the self-drilling fastener device may be used to fasten objects to metals, plastics, composites or wood.

The foregoing and other features of the present invention will become more apparent from the following description and accompanying drawings.

DETAILED DESCRIPTION OF THE PREFERRED EMBODIMENT

Figure 1:
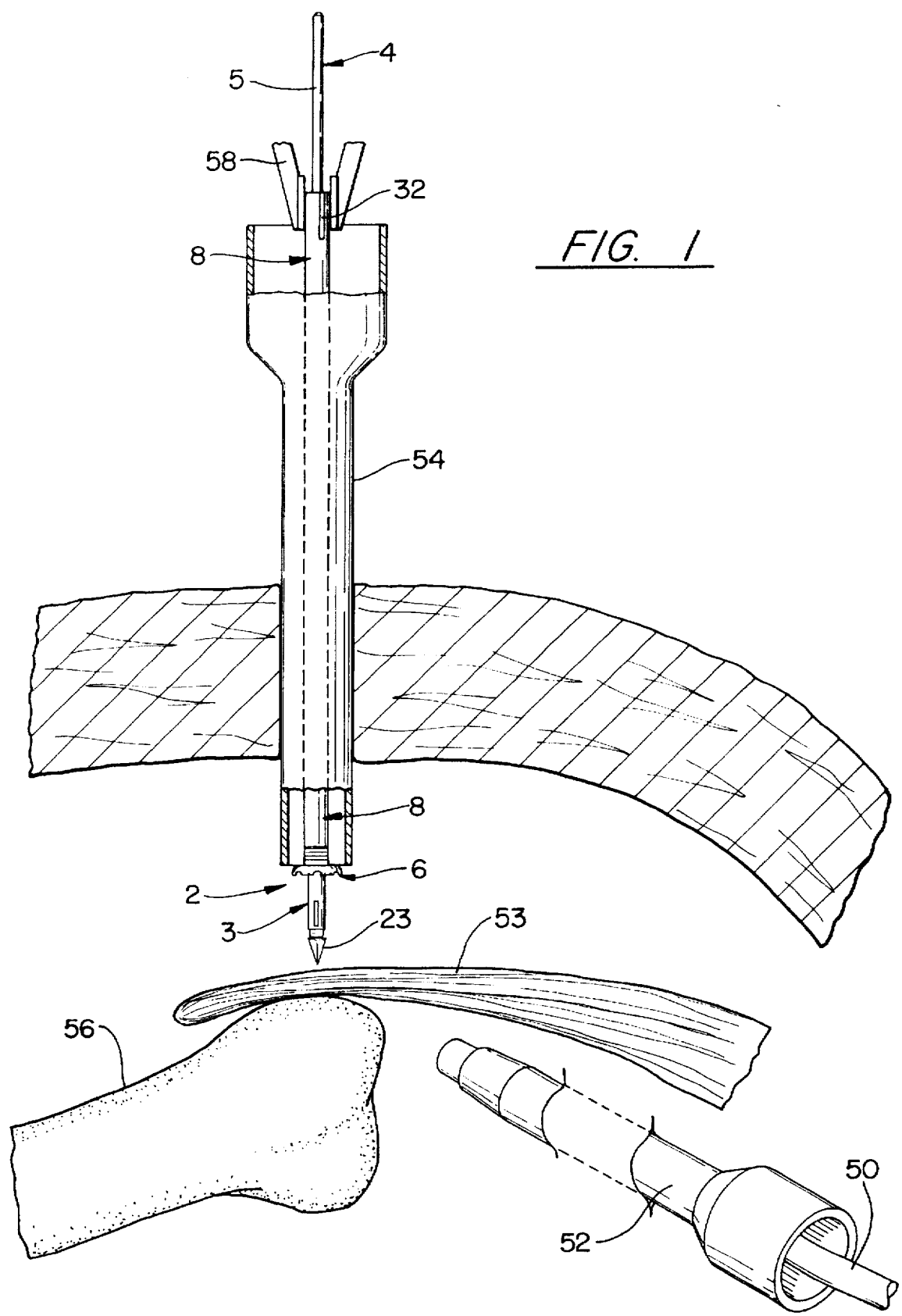
FIG. 1 is a diagrammatic view of a step in an operation using the soft tissue fastener device to attach a ligament to bone during arthroscopic surgery where the surgeon visualizes the detached ligament and has prepared a cavity to see and properly position the ligament on the bone and the fastener device against the ligament.

The same reference numerals depict the same or similar components in all the specifications. The term rivet or rivet-like member as used in this patent application refers to the portion of the assembly that remains in the body and serves to attach the tendon or ligaments to the bone. The term head as used in this patent application refers to the member that comes into contact with the ligament or tendon that is capable of slight rotation in multiple directions in order to align itself with the bone structure.

Figure 6:
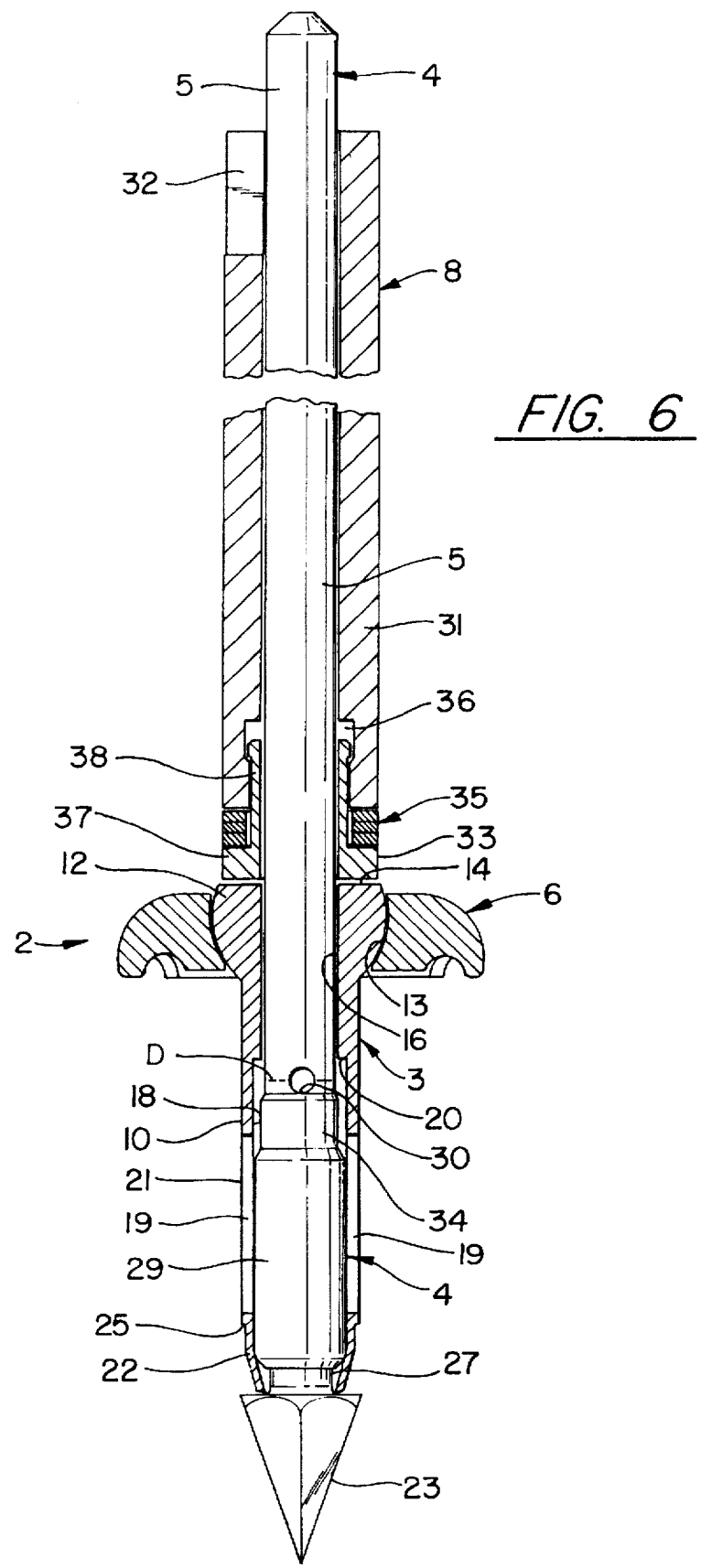
FIG. 6 is a longitudinal sectional view of a soft tissue fastener device.

Referring to FIG. 6, a soft tissue fastener device 2 to fasten soft tissue to bone during an operation is shown having four (4) main parts:

(1) a fastener body 3;
(2) a rotatable head 6 at the top of the fastener body 3;
(3) a drill and puller shaft 4; and
(4) a thrust adapter tube 8.

The fastener body 3 is formed as an annular member 10 for receiving the drill and puller shaft 4. The upper part of the annular member 10 has a spherical flange 12 extending radially outward therefrom forming a ball. The top surface of the spherical flange 12 is made flat at 14 for a purpose to be hereinafter described. The top portion of the fastener body 3 has an opening 16 of a smaller diameter than the opening 18 of the remainder of the fastener body 3. An inner annular step 20 is formed where the two openings 16 and 18 meet for a purpose to be hereinafter described. The lower part of the fastener body 3 is tapered inwardly at 22 to a bottom opening.

Four (4) axial slots 19 are placed lengthwise around the annular member 10 of the fastener body 3 in the lower half thereof to form ribs 21 for a purpose to be hereinafter described. These slots 19 are formed between the annular step 20 and the inward taper at 22. An outer annular step 25 is formed in the lower part of the annular member 10 to control the shape of the ribs 21 as they expand so that the lower portion extends substantially in a radial direction while the upper portion extends downwardly at an angle. This shape slightly compresses the tissue to the bone. The ribs 21 start to bend outwardly at their lower end at 25 and then bend outwardly along the top part of the ribs 21. The annular member 10, comprising the area that becomes the deployed wings, has the lower undercut, annular step 25, positioned such that during deployment, the lower section of the wings attain a position substantially radial to the fastener body 3 while the upper section of the wings deploy to a position extending angularly downward to the lower section. This deployment configuration allows the body 3 of the fastener device 2 to migrate downwardly to cause tightening of the captured ligament between the head 6 of the fastener device 2 and the bone surface. Other deployment configurations can be arrived at if desired. The structure of a specific bone can alter the deployment. However, regardless of bone hardness, the ribs 21 expand in the bone to fix the fastener body 3 in place.

Figure 8:
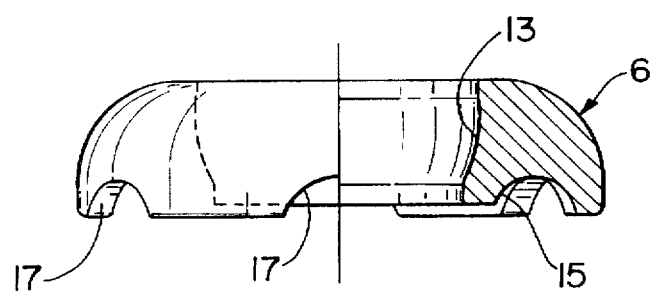
FIG. 8 is a side view of a specific rotatable head for a soft tissue fastener device which can be used.
Figure 9:
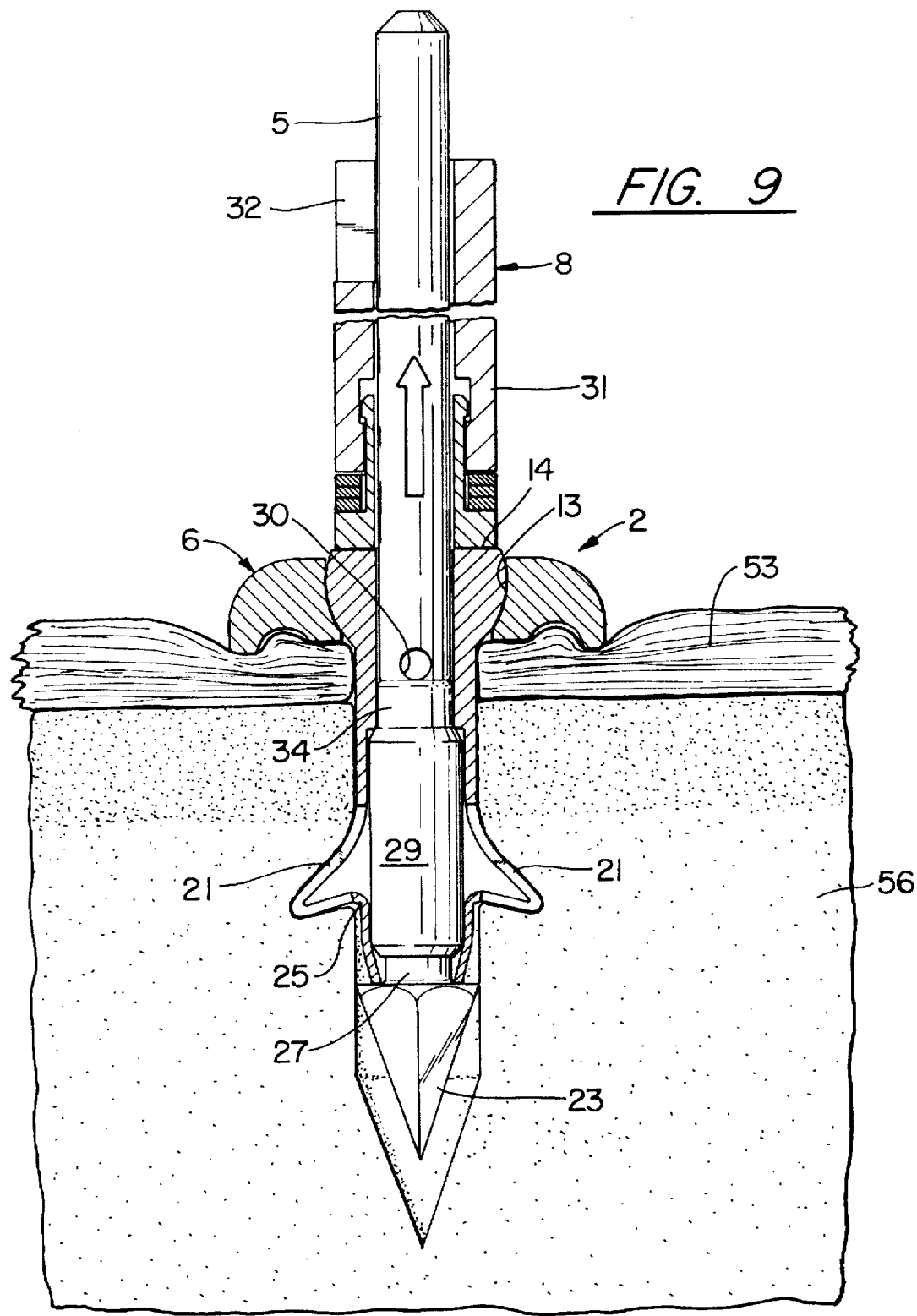
FIG. 9 is a view of the soft tissue fastener device holding a soft tissue (ligament, for example) against the surface of the bone after the use of a surgical puller instrument had caused radial expansion of the fastener body, but prior to the breaking away of the drill and puller shaft from the fastener device.

The rotatable head 6 has a spherical socket 13 which is pressed onto the spherical flange 12 of the annular member 10 so that it cannot fall off. The rotatable head not only rotates about the annular member 10, but is permitted to take angular positions around the annular member 10 to seat properly on tissue with the surface of a bone. The rotatable head 6, as shown in FIG. 8, has an annular groove 15 around the bottom surface of the head 5, along with six (6) short radial grooves 17 from the annular groove 15 to the outer edge, to contact the tissue to capture it with the surface of the bone without traumatizing the tissue. Other configurations of head 6 can be used to capture the tissue.

The drill and puller shaft 4 is assembled with the annular member 10 by having its top end inserted into the bottom opening thereof. The drill and puller shaft 4 has an upper cylindrical rod 5 which, when assembled, extends to a point for controlling by a surgeon when in use. This upper cylindrical rod 5 has a diameter which is slightly smaller than that of opening 16 to permit rotation therein. The lower portion of the drill and puller shaft 4 (see FIG. 6) comprises, from the bottom up, a drill point 23 for drilling into bone; an annular recess 27 for receiving the bottom end of the fastener body 3 where it tapers inwardly at 22; a cylindrical portion 29 having a diameter which is slightly smaller than that of opening 18 to also permit rotation in fastener body 3, but not permit axial entry into opening 16 at annular step 20; cylindrical portion 29 tapers down to a short cylindrical portion 34 which has a snug fig in opening 16; short cylindrical portion 34 tapers down to the diameter of rod 5. a weakened break point is provided on rod 5 at section D, for a purpose to be hereinafter described. The drill point 23 shown is a three-sided solid figure with triangular sides 43 having sharp edges 45 where the sides 43 meet.

The thrust adapter tube 8 is placed over the upper cylindrical rod 5 before the soft tissue fastener device 2 is to be activated to be placed in a position in a bone to fix a soft tissue to a bone.

Figure 7:
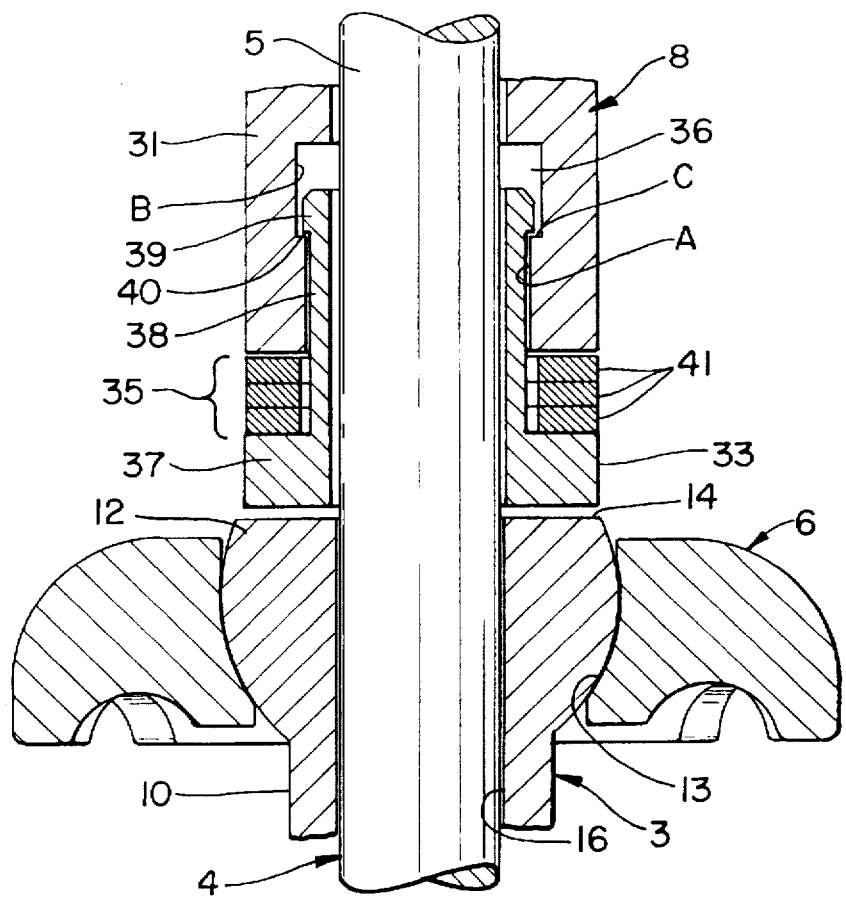
FIG. 7 is an enlarged view of the lower end of the thrust adapter tube showing the thrust bearing means.

The thrust adapter tube 8 comprises a three-part tube (see FIG. 7) having (1) an elongated sleeve 31; (2) a lower end collar 33; and (3) a thrust bearing means 35. The thrust adapter tube 8 extends around the upper cylindrical rod 5 from the top flat surface 14 of the fastener body 3 to just below the top of the upper cylindrical rod 5. The top of the sleeve 31 has a plurality of slits 32 to permit the sleeve 31 to be squeezed in against the upper cylindrical rod 5 so they can be rotated together for drilling. The bottom of the sleeve 31 has the collar 33 mounted thereon for rotational movement and a limited axial movement therebetween.

The bottom of the sleeve 31 has an opening portion 36 extending axially into the sleeve 31. This opening portion 36 has a first entrance section A and a second inner end section B of a larger diameter forming an annular stop C where the two sections meet. The collar 33 has a short tubular section 37 matching the sleeve 31 with a smaller cylindrical section 38 extending upwardly around the cylindrical rod 5 into the opening portion 36 with an enlarged diameter annular end 39 forming an annular stop 40.

The thrust bearing means 35 is allocated between the bottom of the sleeve 31 and the facing annular surface of the short tubular section 37 of the collar 33. This thrust bearing means 35 comprises three (3) bearing rings 41 to permit the sleeve 31 to rotate without rotating the collar 33 so as not to rotate the fastener body 3. The thrust adapter tube 8 supports the drill and puller shaft 4 during drilling to prevent bending of the upper cylindrical rod 5.

It can be seen that a limited axial movement downwardly of the collar 33 with the sleeve 31 extends to the contact of the stops C and 40 and presents an annular space for the thrust bearing means 35. During fabrication of the thrust adapter tube 8, the thrust bearing means 35 (the three (3) bearing rings 41) is placed over the smaller cylindrical section 38 and the enlarged diameter annular end 39 is pressed into the smaller entrance section A of the opening 36 until it reaches the larger section B where axial movement is permitted. The thrust bearing means 35 allows for a small free movement before it is contacted by both the bottom of the sleeve 31 and the facing annular surface of the short tubular section 37 of the collar 33.

Generally, tendons and ligaments which have become detached must be repaired surgically. Access to the injured part is made through an incision in the overlying skin. More frequently, if the injury is around a large joint, such as the knee or shoulder, visualization of the injured area can be achieved through a very small (½") incision with the aid of an arthroscope. The arthroscope is a tubular instrument which provides a source of light through a fiberoptic cable and transmits a magnified image of the injured part through a series of lenses to a television screen. Once the desired part has been visualized, the surgeon may make other small incisions near the injured part to allow access for other specialized instruments which can probe, cut, or otherwise manipulate the tissues. The access tunnels or portals are generally maintained by a rigid tube (cannula) so that the arthroscope and the instruments can be removed and easily replaced or exchanged without having to make new incisions.

Figure 2:
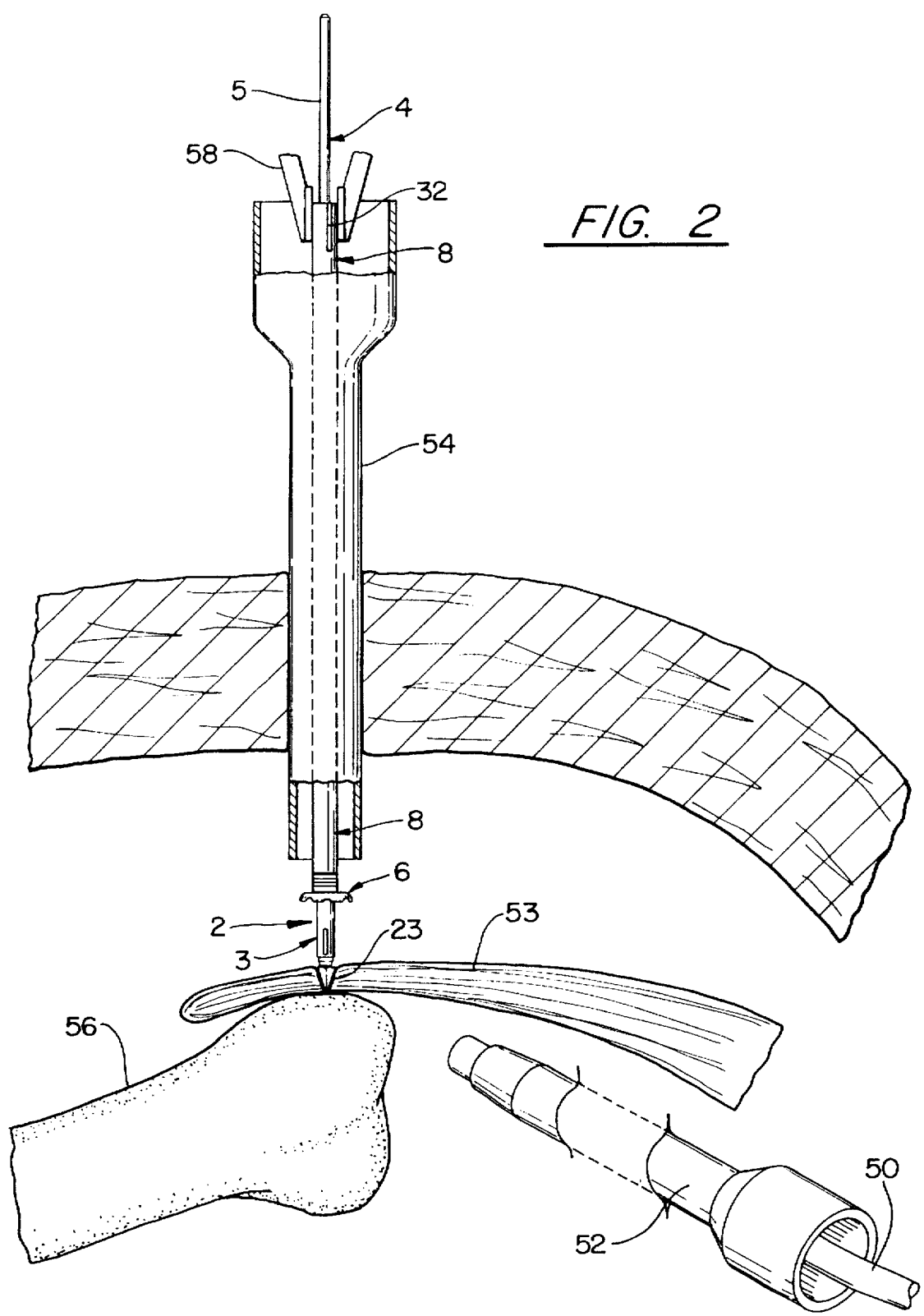
FIG. 2 is a diagrammatic view of another step in an operation using the soft tissue fastener device where the ligament is placed in its proper position on the bone and the soft tissue fastener device has its drill point in position impaling the ligament, with the drill point ready to be rotated to advance into the bone.
Figure 3:
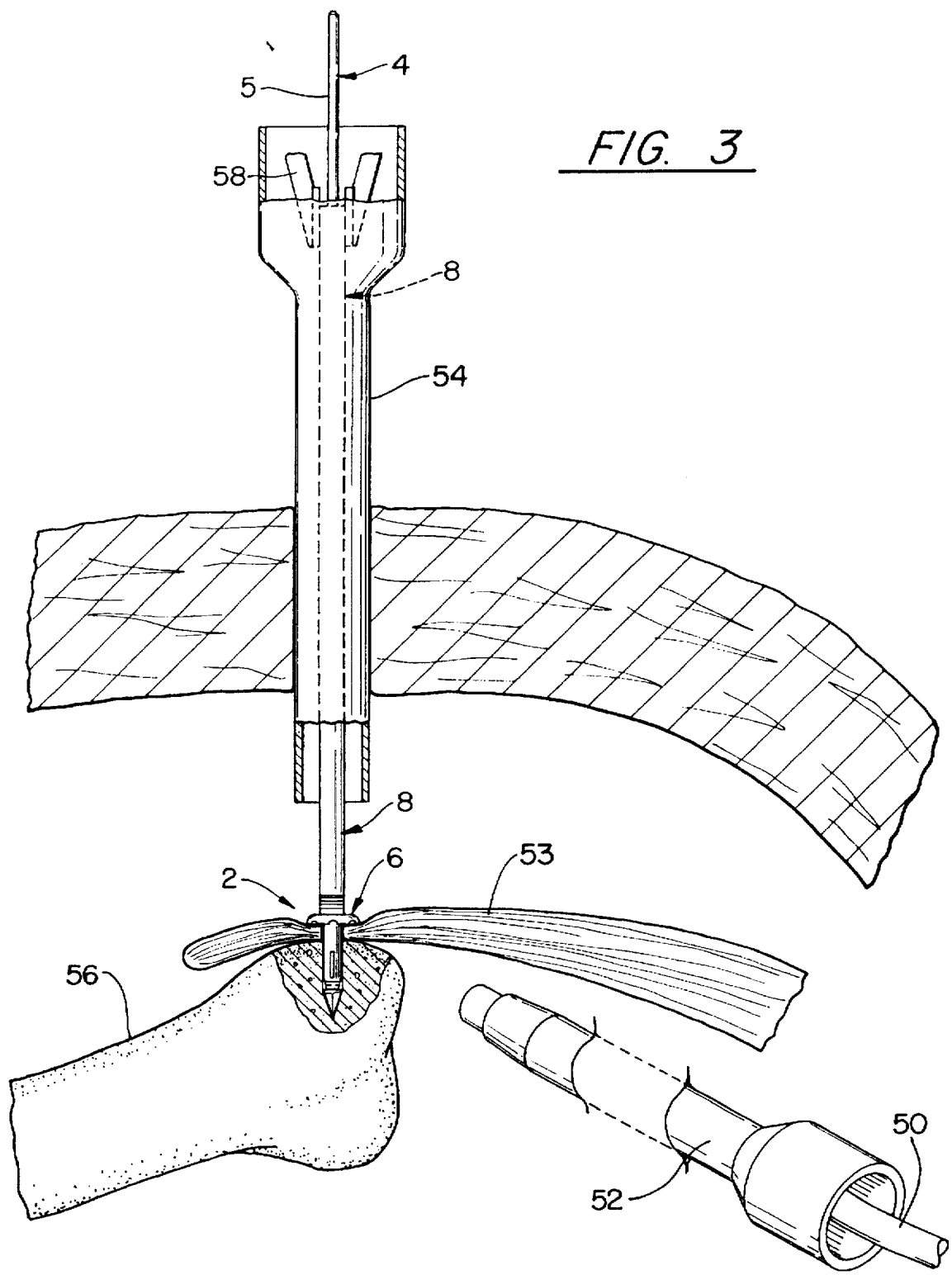
FIG. 3 is a diagrammatic view of another step in the operation using the soft tissue fastener device where the holding device of a drill is placed on the free ends of the thrust adapter and the drill and puller shaft of the soft tissue fastener device to hold them together and rotate them to have the drill point advance into the bone to properly position the rotatable head to place the soft tissue against the bone.
Figure 4:
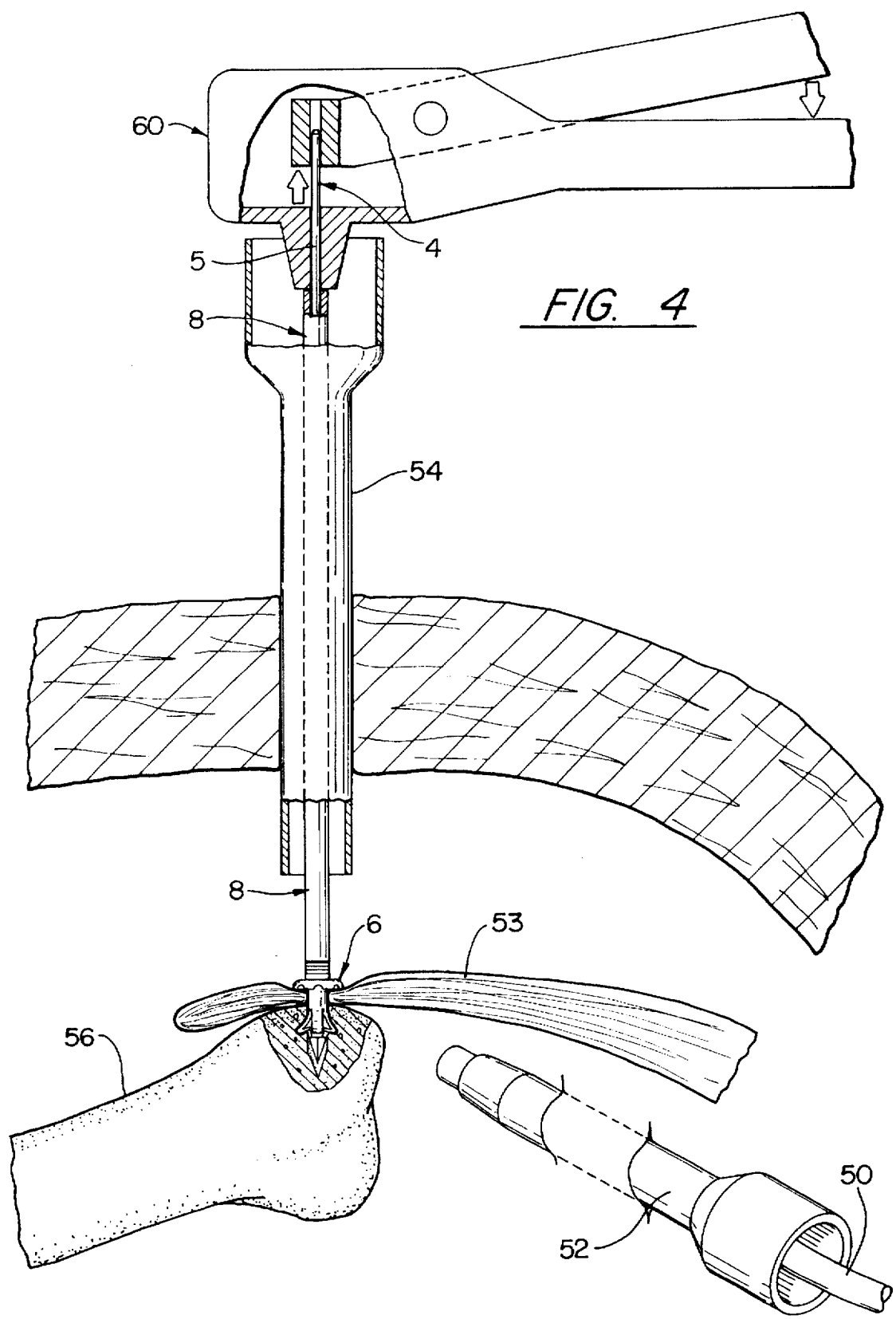
FIG. 4 is a diagrammatic view of another step in an operation using the soft tissue fastener device where the drill and holding device is removed and a surgical puller instrument is placed over the protruding drill and puller shaft and against the top of the thrust adapter to pull the drill and puller shaft to cause radial expansion of the fastener body into the bone to fix the soft tissue in place. In this step, the drill and puller shaft is broken away from the fastener device at the weakened break-away point when the fastener body is fixed in the bone.
Figure 5:
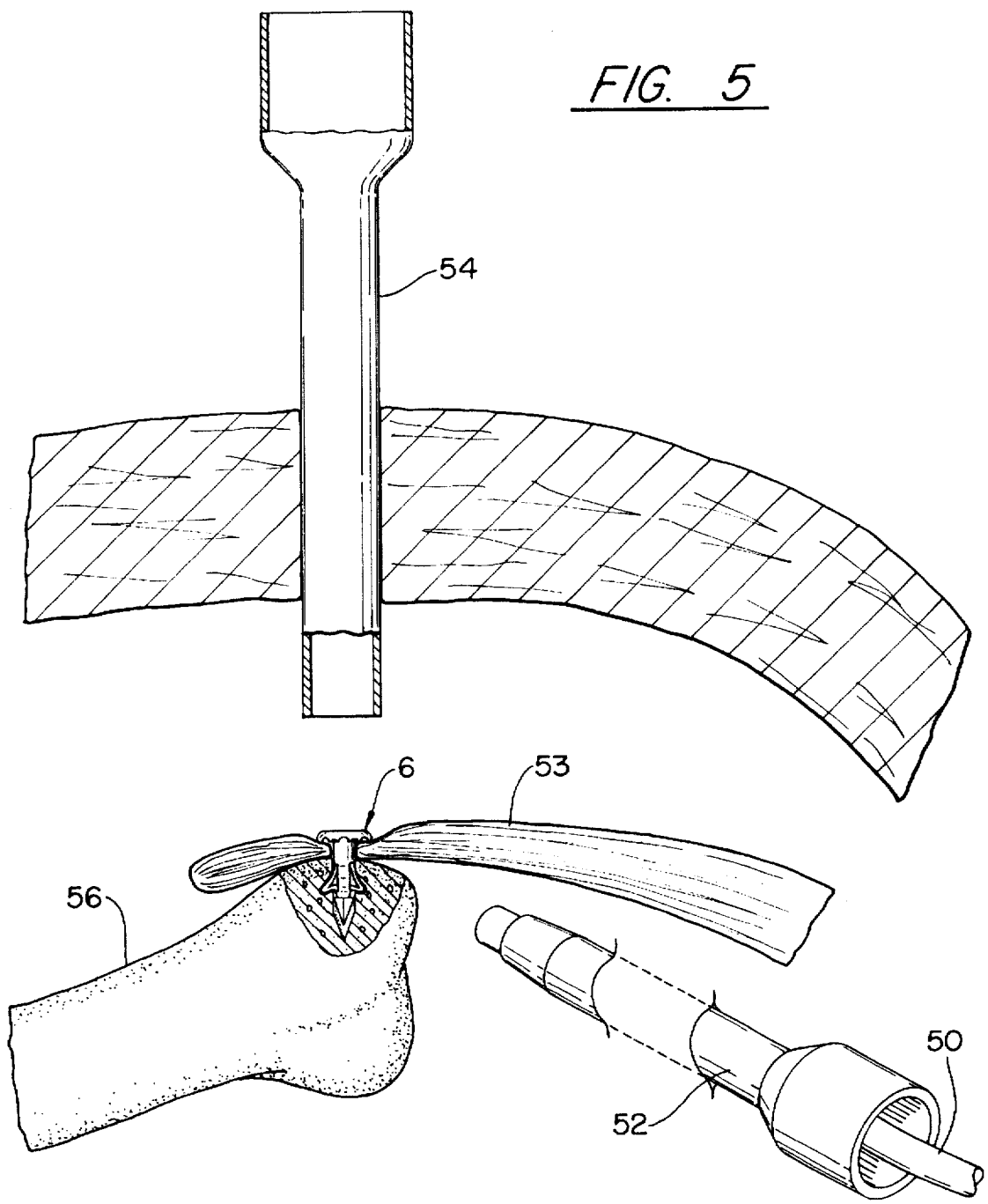
FIG. 5 is a diagrammatic view of another stp in an operation using the soft tissue fastener device where the surgical puller instrument has been removed along with the broken away part of the drill and puller shaft and the thrust adapter.

Using the disclosed technique herein (see FIGS. 1–4), the surgeon visualizes the detached tissue, tendon or ligament, with the arthroscope 50 through a cannula 52. A second incision is then made over the injured part and a cannula 54 is inserted providing access to the injured part. The cannula is freely mobile in the small incision. The fastener device 2 is passed through the cannula 54. The detached end of the ligament, or tendon, 53 is then impaled on the sharp drill point 23 of the drill and puller shaft 4 of the fastener device 2. The surgeon may then manipulate the fastener device 2 with the impaled ligament, or tendon, 53 to its proper position on the bone (see FIG. 2). The drill point 23 is placed against the bone 56. The outer ends of the thrust adapter tube 8 and the drill and puller shaft 4 of the fastener device 2 are secured in a Jacob Chuck, or other holding device 58, of a drill external to the skin. The drill is activated by the surgeon; the drill point 23 advances into the bone 56 until the ligament, or tendon, 53 is seen to be seated flush against the surface of the bone 56 by the rotatable head 6 (see FIG. 3) as desired. If the drill point 23 enters the bone at a slight angle, the head 6 can adjust to seat properly on the bone. At this point, the drill is removed from the fastener device 2. The surgeon places a surgical puller instrument 60 over the protruding drill and puller shaft 4 and against the tope of the thrust adapter tube 8 (see FIG. 4). The surgical puller instrument 60 grips the drill and puller shaft 4 and pulls it axially outwardly while the top of the fastener body 2 is held in place by the thrust adapter tube 8 over the drill and puller shaft 4.

As can be seen, the outward pull is countered by the contact between the outer end of the thrust adapter tube 8 and the surgical puller instrument 60. The inner end of the thrust adapter tube 8, collar 33, is seated on the flat surface 14 of the fastener body 3. Thus, the fastener body 3 is compressed between the top of the drill point 23 of the drill and puller shaft 4 and the inner end of the thrust adapter tube 8, collar 33. Compression of the fastener body 3 causes radial expansion of the ribs 21 of the fastener body 3. Once maximal radial expansion occurs, the drill and puller shaft 4 should break away at predetermined weakened section D along its length due to the resistance of the drill and puller shaft 4 to the outward pull of the surgical puller instrument 60. The section D is weakened by a hole 30 placed at section D through the drill and puller shaft 4. If this action does not break the drill and puller shaft 4 off at weakened section D, when the cylindrical portion 29 of the drill and puller shaft 4 reaches opening 16 at annular step 20, the drill and puller shaft 4 will break off at weakened section D. The radially expanded fastener body 3 is now larger in diameter than the hole drilled in the surface of the bone 56 and therefore is secured within the bone. The ligament, or tendon, 53 is secured to the surface of the bone 56 by the rotatable head 6.

The subject matter of U.S. Pat. No. 5,326,205 and U.S. application Ser. No. 08/215,279, dated Mar. 21, 1994, is included herein by reference as if it were fully set forth.

Figure 10:
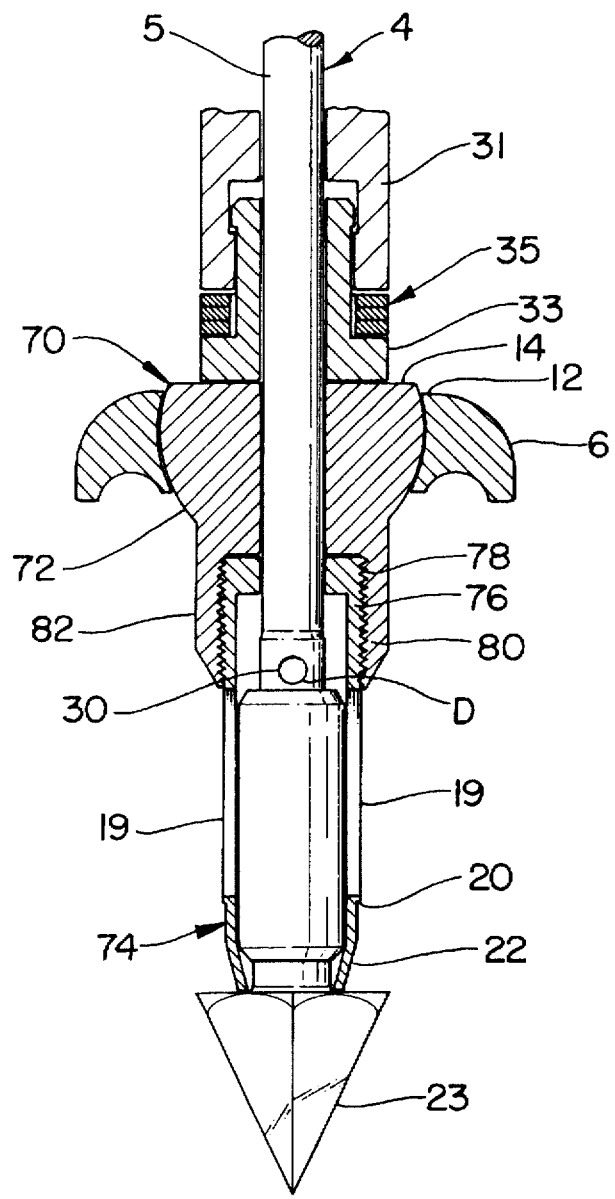
FIG. 10 is a fragmentary sectional view in elevation illustrating another embodiment of this invention.
Figure 11:
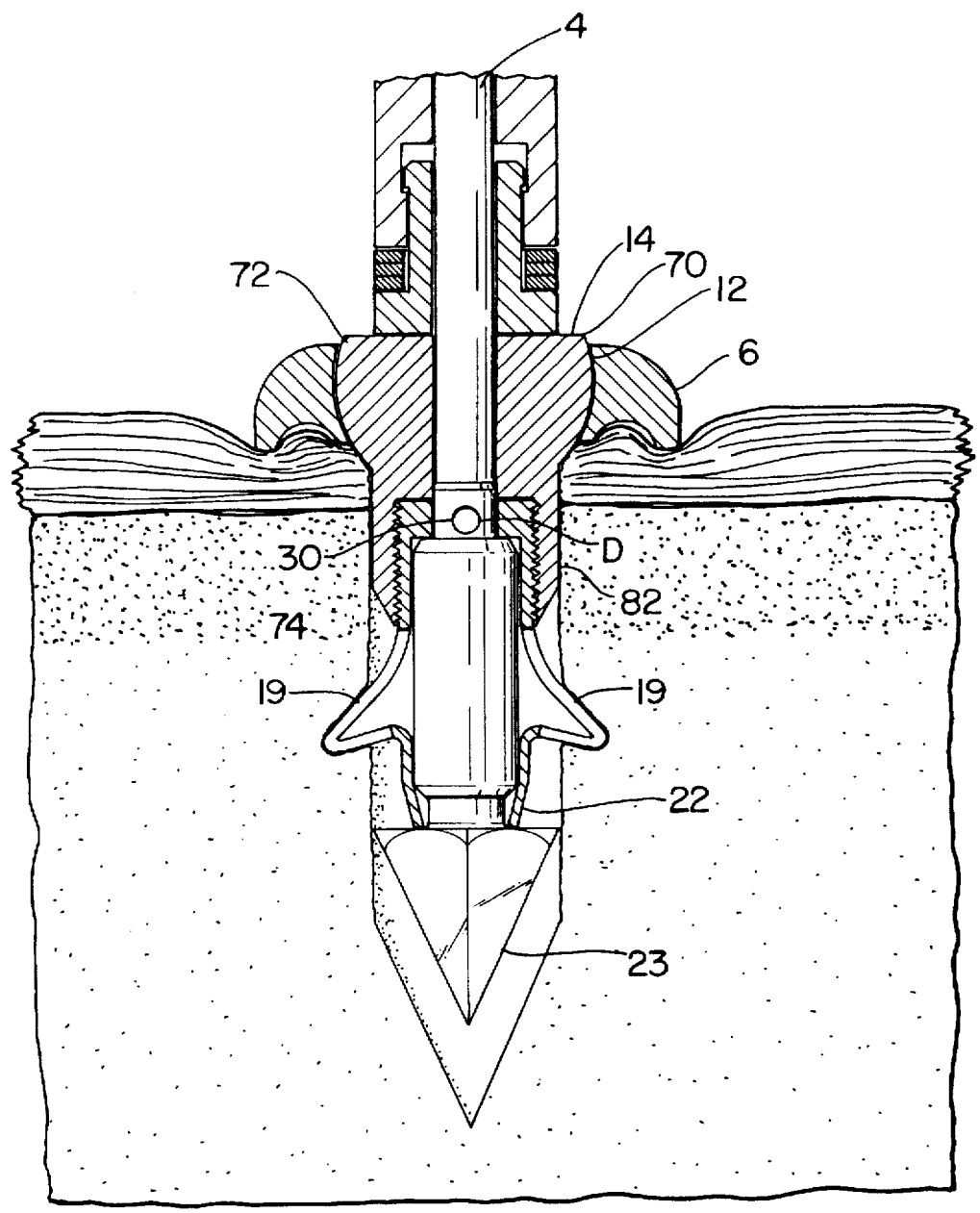
FIG. 11 is a fragmentary sectional view in elevation illustrating the with the fastener inserted into the bone and the soft tissue being attached thereto.

In accordance with this invention as can best be seen by referring to FIGS. 10 and 11 the rivet-like fastener is formed in four components, namely, the drill and puller shaft 4, the head 6 and the annular fastener body 70 which is formed in two components, the socket portion 72 and the rivet portion 74. The socket portion 72 and rivet portion 74 of the fastener body 70 have a central opening similar to that described in connection with annular member 10 for receiving the drill and puller shaft 4. The socket portion 72 has a spherical flange 12 extending radially outward therefrom forming a ball. The rivet portion 74 the fastener body 70 is tapered inwardly at 22 to a bottom opening.

A plurality of axial slots 19 are placed lengthwise around the rivet portion 74 of the fastener body 70 to form ribs 21. These slots 19 are formed between the annular step 20 and the inward taper at 22. The functioning of the rivet portion and head portion is identical to the functioning of the lower portion of the annular member 10 and the upper portion of annular member 10 and head 6 described in connection with the other embodiments. The upper portion 76 of the rivet portion 74 is annular in shape and is threaded at 78 to mate with the internal threads 80 formed on the lower portion 82 of socket portion 74. As is apparent from the Figs. the top end of the rivet portion 74 extends beyond section D. This is to assure that the break line when the drill and puller shaft is sheared the portion of that drill and puller shaft remaining in the body doesn't project beyond the top end of the rivet portion 74. According to this invention the rivet portion 74 is made from a surgical metallic material such as an implantable grade of titanium or an alloy thereof and the socket portion 72 is made from a bioabsorbable polymer material. The two components are screwed together to form an integral unit.

Figure 13:
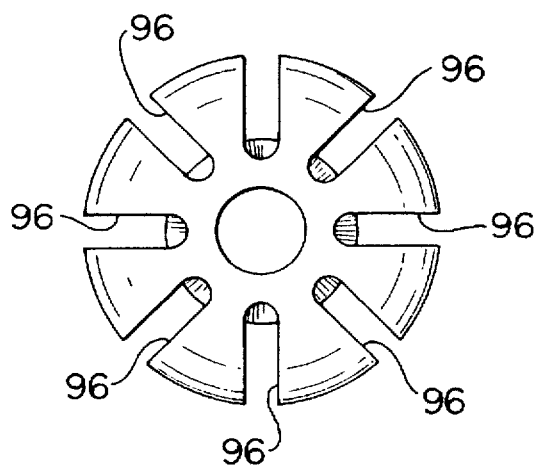
FIG. 13 is a top plan view illustrating a modified head made in accordance with this invention.
Figure 12:
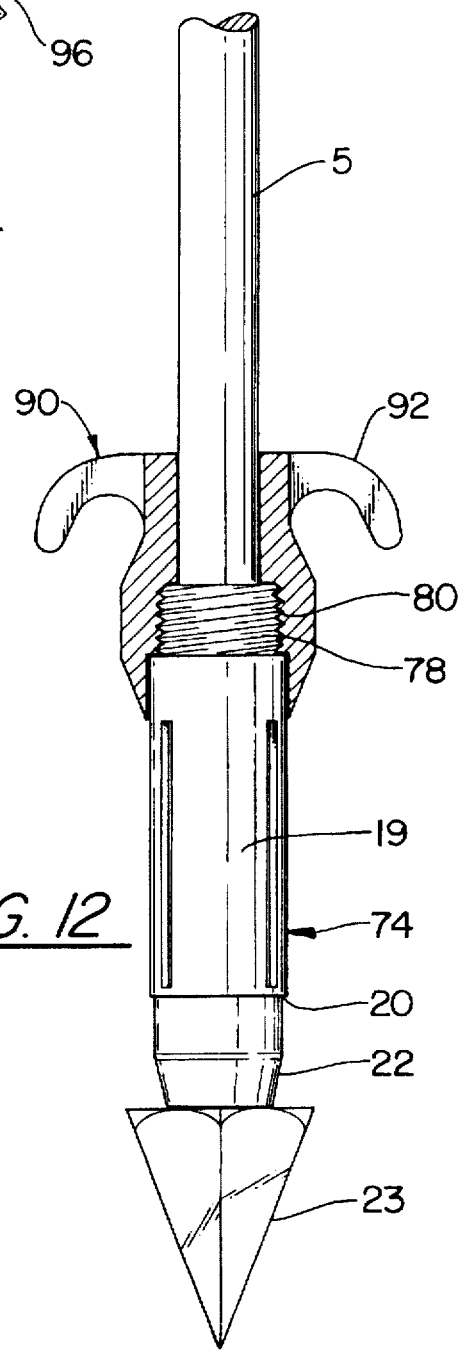
FIG. 12 is a partial view in section and elevation exemplifying another embodiment of this invention.

FIGS. 12 and 13 discloses a modification to the swivel head depicted in all the other embodiments, which modification can be utilized with the other soft tissue fastener devices. In this modification the head 6 and socket member 70 is replaced by an integral holding unit 90 that combines the function of the swivel head arrangement depicted in the other embodiments. The upper portion of the integral holding unit 90 is formed of a circular disk-like element 92 where the lower portion designated as the projecting portion 94 is identical to the portion 82 of socket member 72 depicted in FIG. 10. The circular disk-like element 92 is formed with a plurality of equally spaced radially extending slits 96 that form holding fingers or pedals 98 therebetween. The fingers 98 are flexible and since each of the fingers can be flexed individually they will conform to the configuration of the surface of the host bone structure underlying each of the fingers. Similarly to the embodiment described in connection with FIGS. 10 and 11, the integral holding unit 90 is made from a bioabsorbable polymer material and the rivet portion 74 is made from an implantable grade titanium or an alloy thereof.

While the principles of the invention have now been made clear in an illustrative embodiment, it will become obvious to those skilled in the art that many modifications in arrangement are possible without departing from those principles. The appended claims are, therefore, intended to cover an embrace any such modifications, within the limits of the true spirit and scope of the invention.

We claim:

1. An expandable fastener device for attaching soft body tissue to bone, said fastener device having an annular body, head means for affixing said soft body tissue to the bone made from a bioabsorbable polymer material being attached to the top of said annular body for contacting the soft body tissue, a shaft extending through said head means and said annular body, said shaft having a drill point below said annular body for extending through the soft tissue and drilling in bone for placing the soft body tissue against the bone, said annular body being expandable radially into the bone when compressed for fixing said annular body in place and said drill point and said shaft, drill point and said annular body being made from a surgical metallic material, said head having internal threads formed in a recess formed therein and said annular body having external threads complementing said internal threads and being in threadable engagement therewith.

2. An expandable fastener device as set forth in claim 1 wherein said head swivels on said annular body.

3. An expandable fastener device as set forth in claim 1 wherein said head is mounted for angular movement with said annular body.

4. An expandable fastener device as set forth in claim 1 wherein said head has a bottom portion with grooves to accept tissue to fix to bone.

5. An expandable fastener device as set forth in claim 1 wherein the top of said annular body is formed as a spherical joint with the head permitting rotation and angular movement of said head in relation with said annular body.

6. An expandable fastener device as set forth in claim 1 wherein said shaft is elongated for remote rotational actuation.

7. An expandable fastener device as set forth in claim 6 wherein a thrust adapter tube is positioned around said elongated shaft to support the shaft against bending.

8. An expandable fastener device as set forth in claim 6 wherein a thrust adapter tube is positioned around said elongated shaft to rotate said elongated shaft without rotating said annular body.

9. An expandable fastener device as set forth in claim 8 wherein the top of said annular body is flat to receive the bottom of the thrust adapter tube.

10. An expandable fastener device as set forth in claim 9 wherein the bottom of the thrust adapter tube has a thrust bearing means to prevent rotation of the bottom of the thrust adapter tube when the thrust adapter tube is rotating and the bottom of the thrust adapter tube is against the top of said annular body.

11. An expandable fastener device as set forth in claim 1, said annular body being expandable radially into the bone by axial movement of said shaft, said shaft having a break point where the upper part breaks off when the annular body is fixed in place.

12. An expandable fastener device as set forth in claim 11 wherein said break point is formed in said shaft by a hole placed through said shaft.

13. An expandable fastener device as set forth in claim 1 wherein the bottom portion of said annular body has lengthwise slots located therein with ribs therebetween, said ribs extending as radial arms when said annular body is compressed lengthwise.

14. An expandable fastener device as set forth in claim 13 wherein said slots and ribs have upper and lower ends, said annular body having a wall of reduced thickness extending downwardly below the lower end of the slots.

15. An expandable fastener device as claimed in claim 1 wherein said head includes a disk-like member having a plurality of radially extending slits formed therein to form spaced fingers that are deformable to conform to the shape of the host bone underlining each of said fingers.

* * * * *